United States Patent
Kang et al.

(10) Patent No.: US 11,098,004 B2
(45) Date of Patent: Aug. 24, 2021

(54) METHOD OF PURIFYING 1,5-DIAMINOPENTANE

(71) Applicant: CJ CHEILJEDANG CORPORATION, Seoul (KR)

(72) Inventors: Seok Hyun Kang, Yongin-si (KR); Won Sik Gwak, Yongin-si (KR); Chang Yub Oh, Yongin-si (KR); Jin Tae Hong, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/646,651

(22) PCT Filed: Oct. 8, 2018

(86) PCT No.: PCT/KR2018/011828
§ 371 (c)(1),
(2) Date: Mar. 12, 2020

(87) PCT Pub. No.: WO2019/078528
PCT Pub. Date: Apr. 25, 2019

(65) Prior Publication Data
US 2020/0270198 A1    Aug. 27, 2020

(30) Foreign Application Priority Data
Oct. 18, 2017 (KR) .................. 10-2017-0135232

(51) Int. Cl.
*C07C 209/84* (2006.01)
*B01D 3/14* (2006.01)
(Continued)

(52) U.S. Cl.
CPC ............ *C07C 209/84* (2013.01); *B01D 3/148* (2013.01); *C07C 211/09* (2013.01); *C12P 13/001* (2013.01)

(58) Field of Classification Search
None
See application file for complete search history.

(56) References Cited

U.S. PATENT DOCUMENTS 8,785,695 B2    7/2014   Vlkert et al.
9,963,421 B2    5/2018   Gwak

FOREIGN PATENT DOCUMENTS

CN    102056889 B    1/2016
CN    105658802 A    6/2016
(Continued)

OTHER PUBLICATIONS

Kind, S., et al., "Bio-based Production of the Platform Chemical 1.5-diaminopentane", Applied Microbiology and Biotechnology, (electronic publication)Jul. 15, 2011, vol. 91, pp. 1287-1296.
(Continued)

*Primary Examiner* — Amy C Bonaparte
(74) *Attorney, Agent, or Firm* — Cantor Colburn LLP (57) ABSTRACT

Provided is a method of refining 1,5-diaminopentane, the method including preparing a fermented broth including a carbonate salt of 1,5-diaminopentane; preparing a first composition by heating the fermented broth; preparing a second composition and an evaporation residue by evaporating the first composition; preparing a third composition by adding water to the evaporation residue and evaporating the water; and recovering 1,5-diaminopentane by distilling the second composition and the third composition.

8 Claims, 4 Drawing Sheets

(51) Int. Cl.
*C07C 211/09* (2006.01)
*C12P 13/00* (2006.01)

(56) References Cited

FOREIGN PATENT DOCUMENTS

| | | | |
|---|---|---|---|
| JP | 2005006650 A | | 1/2005 |
| JP | 2008193898 A | | 8/2008 |
| JP | 5548864 B2 | | 12/2010 |
| JP | 2011225554 | * | 11/2011 |
| JP | 2015096552 A | | 5/2015 |
| JP | 2016522681 A | | 8/2016 |
| KR | 101457229 B1 | | 11/2014 |
| KR | 1020150115533 | | 10/2015 |
| KR | 101579994 B1 | | 12/2015 |
| KR | 1020160131687 A | | 11/2016 |
| WO | 2007113127 A1 | | 10/2007 |
| WO | 2009092793 A2 | | 7/2009 |
| WO | 2010002000 A1 | | 1/2010 |
| WO | WO-2010002000 A1 | * | 1/2010 ........... C07C 209/84 |
| WO | 2014113999 A1 | | 7/2014 |
| WO | 2014114000 A1 | | 7/2014 |

OTHER PUBLICATIONS

Office Action dated Jan. 20, 2020 issued in KR Patent Application No. 10-2017-0135232.
Office Action dated Apr. 23, 2019 issued in KR Patent Application No. 10-2017-0135232.
Office Action dated Sep. 27, 2018 issued in KR Patent Application No. 10-2017-0135232.
Office Action dated Jul. 19, 2019, issued in corresponding TW Patent Application No. 107136387, and English Translation.
Second Office Action dated Oct. 31, 2019, issued in corresponding TW Patent Application No. 107136387 with English Translation.
International Search Report dated Mar. 22, 2019, issued in Corresponding PCT/KR2018/011828 3pp.
English Translation of International Search Report dated Mar. 22, 2019, issued in Corresponding PCT/KR2018/011828 2pp.
English Translation of Office Action dated Mar. 22, 2021 issued in Japanese Patent Application No. 2020-518707, which corresponds to the above-identified application.
Office Action dated Mar. 22, 2021 issued in Japanese Patent Application No. 2020-518707, which corresponds to the above-identified application.
English Translation of JP 2015096552, May 21, 2015.
Extended European Search Report dated Jun. 24, 2021 of European Patent application No. 18869252.9, which corresponds to the above-identified application.

* cited by examiner

METHOD OF PURIFYING 1,5-DIAMINOPENTANE

This application is a national stage application of PCT/KR2018/011828 filed Oct. 8, 2018, which claims priority to Korean Patent Application No. 10-2017-0135232 filed on Oct. 18, 201, both/all of which are hereby incorporated by reference in their entirety.

TECHNICAL FIELD

One or more embodiments relate to a method of refining 1,5-diaminopentane.

BACKGROUND ART 1,5-diaminopentane (cadaverine) is an important base chemical in industrial applications and may be used as an additive or as a component of polymers such as polyamides or polyurethanes through polymerization processes. 1,5-diaminopentane may be produced by chemical or biological methods. Specifically, the biological methods may be classified into a method of producing 1,5-diaminopentane through enzymatic decarboxylation after L-lysine microbial cultivation (Japanese Laid-Open Patent Application No. 2005-006650) or a method of producing 1,5-diaminopentane by culturing a microorganism that produces 1,5-diaminopentane (Korean Patent Registration No. 10-1457229 and Japanese Patent No. 5548864). When biological methods are used to ferment 1,5-diaminopentane using microorganisms, large amounts of organic acid and acetic acid are produced. Failure to remove organic acid from 1,5-diaminopentane is a major cause of reduced polymerization, since amide bonds form between amine groups and organic acid in a polymerization reaction for the production of secondary products such as polyamide and polyurethane. Therefore, 1,5-diaminopentane produced through fermentation requires the addition of a large amount of an alkaline compound to increase the purity and yield, and as a result, by-product treatment and additional refining are required.

Therefore, a method of effectively refining 1,5-diaminopentane from a fermented broth is required.

DESCRIPTION OF EMBODIMENTS

Technical Problem

One or more embodiments include a method of refining 1,5-diaminopentane, the method including preparing a fermented broth including a carbonate salt of 1,5-diaminopentane; preparing, by heating the fermented broth, a first composition in which the carbonate salt of 1,5-diaminopentane is thermally decomposed; preparing a second composition and an evaporation residue by evaporating the first composition; preparing a third composition by adding water to the evaporation residue and evaporating the water; and recovering 1,5-diaminopentane by distilling the second composition and the third composition.

Solution to Problem

One or more embodiments include a method of refining 1,5-diaminopentane, the method including preparing a fermented broth including a carbonate salt of 1,5-diaminopentane; preparing, by heating the fermented broth, a first composition in which the carbonate salt of 1,5-diaminopentane is thermally decomposed; preparing a second composition and an evaporation residue by evaporating the first composition; preparing a third composition by adding water to the evaporation residue and evaporating the water; and recovering 1,5-diaminopentane by distilling the second composition and the third composition.

Advantageous Effects of Disclosure

When a method of refining 1,5-diaminopentane according to one or more embodiments is used, 1,5-diaminopentane with a high purity may be obtained at a high yield.

BEST MODE

Figure 1:
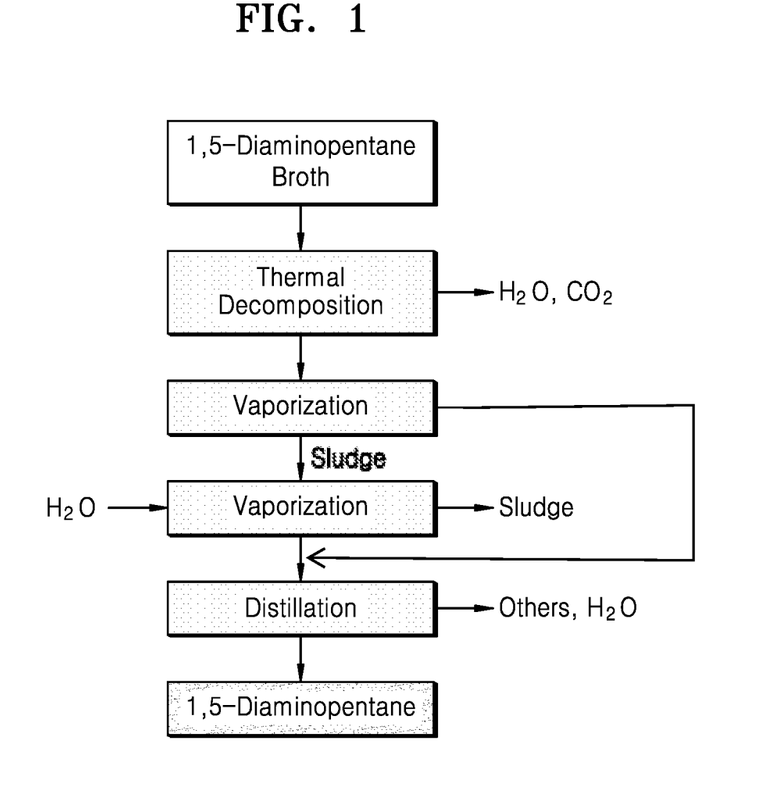
FIG. 1 shows a flowchart of a method of refining 1,5-diaminopentane, according to one or more example embodiments.
Figure 2:
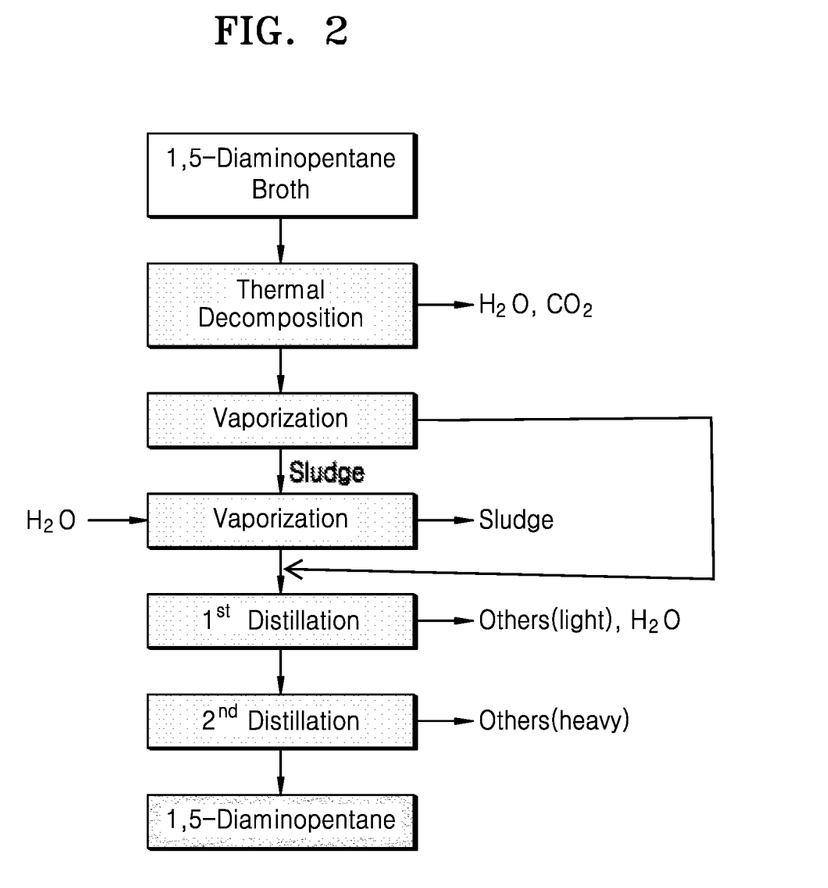
FIG. 2 shows a flowchart of a method of refining 1,5-diaminopentane, according to Example 1.
Figure 3:
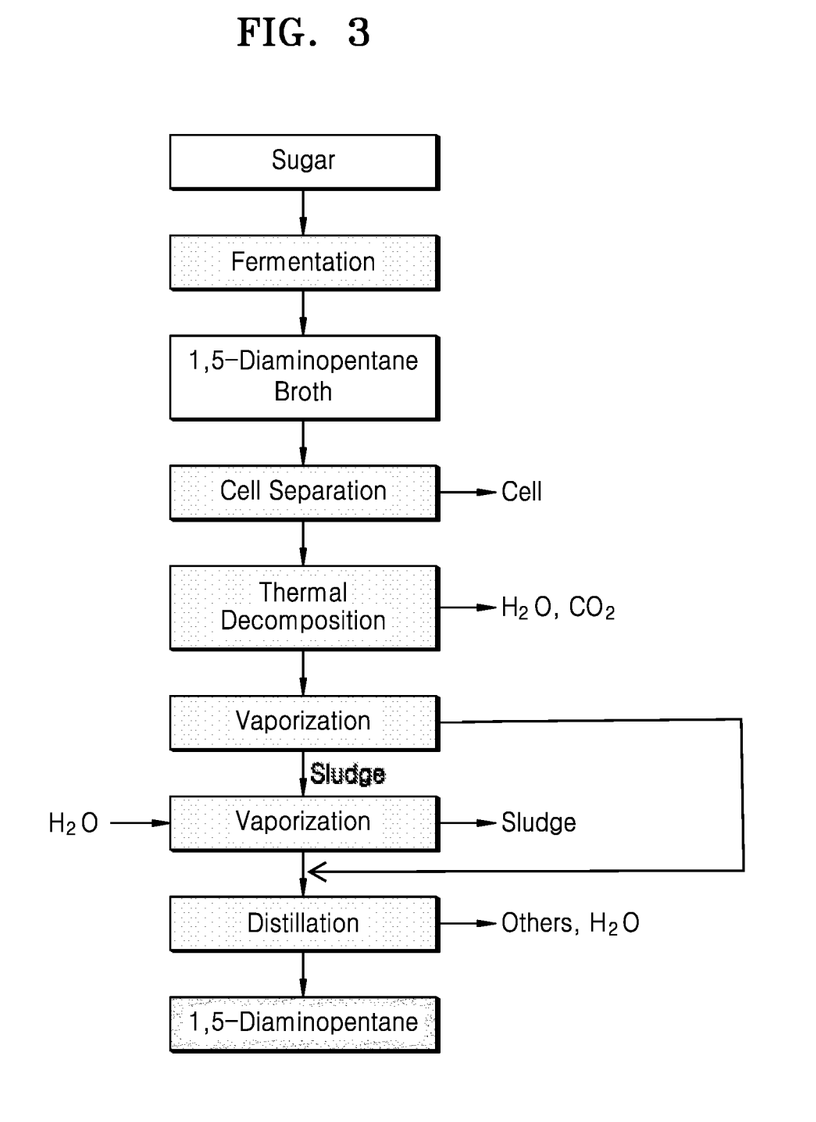
FIG. 3 shows a flowchart of the preparation of a fermented broth in FIG. 1 in detail.
Figure 4:
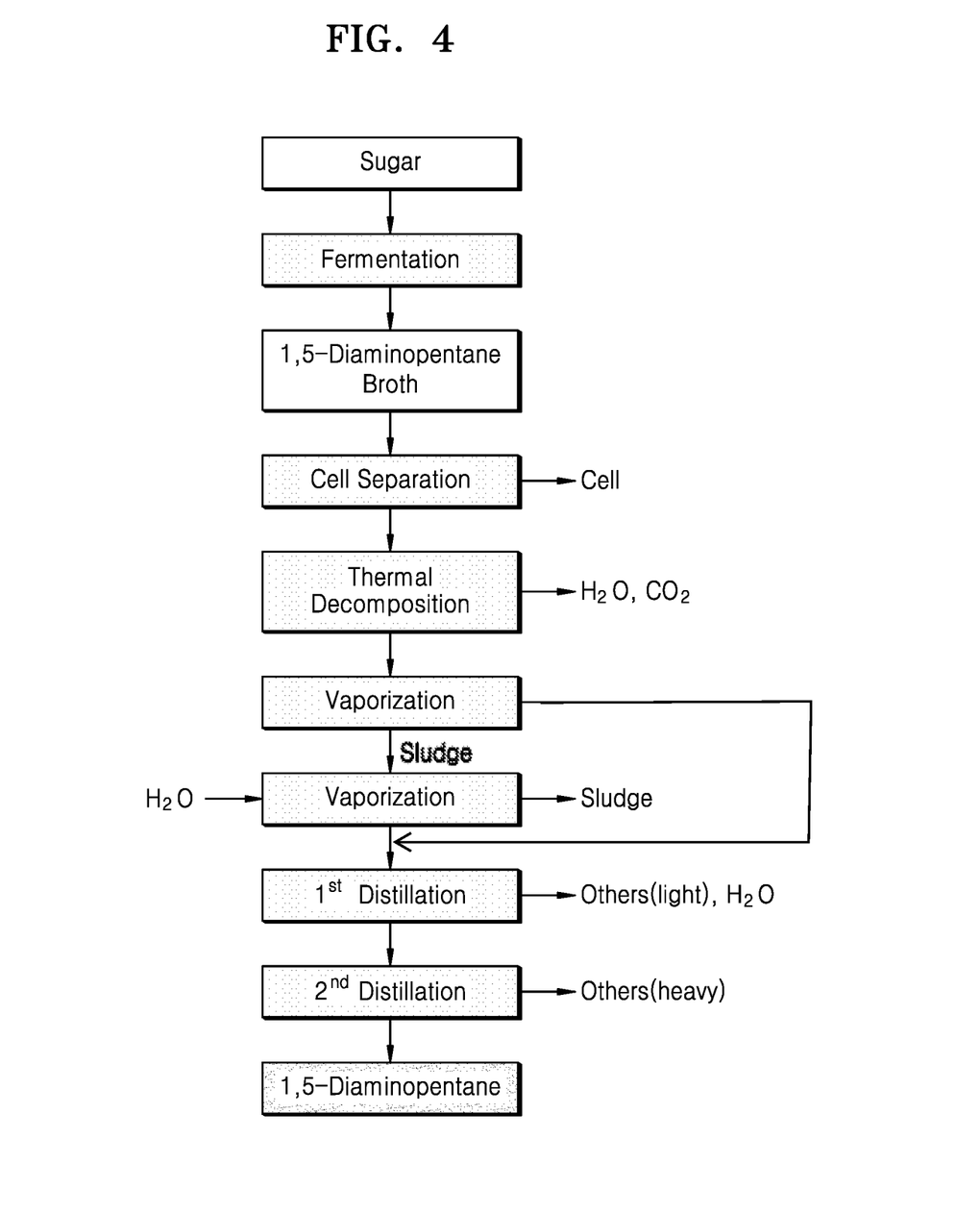
FIG. 4 shows a flowchart of the preparation of a fermented broth in FIG. 2 in detail.

As the inventive concept allows for various changes and numerous embodiments, particular embodiments will be illustrated in the drawings and described in detail in the written description. However, this is not intended to limit the inventive concept to particular modes of practice, and it is to be appreciated that all changes, equivalents, and substitutes that do not depart from the spirit and technical scope of the inventive concept are encompassed in the inventive concept.

While such terms as "first," "second," "third," "fourth, or the like, may be used to describe various components, such components must not be limited to the above terms. The above terms are used only to distinguish one component from another.

According to one or more embodiments, a method of refining 1,5-diaminopentane may include preparing a fermented broth including a carbonate salt of 1,5-diaminopentane; preparing, by heating the fermented broth, a first composition in which the carbonate salt of 1,5-diaminopentane is thermally decomposed; preparing a second composition and an evaporation residue by evaporating the first composition; preparing a third composition by adding water to the evaporation residue and evaporating the water; and recovering 1,5-diaminopentane by distilling the second composition and the third composition.

The preparing of a fermented broth including a carbonate salt of 1,5-diaminopentane may be preparing a fermented broth including a carbonate salt of 1,5-diaminopentane obtained by fermentation of microorganisms.

The term 'carbonate salt of 1,5-diaminopentane', as used herein, refers to at least one selected from 1,5-diaminopentane carbonate and 1,5-diaminopentane bicarbonate. However, embodiments are not limited thereto. Any suitable compound formed by binding of 1,5-diaminopentane and carbonate ions in a fermented broth may be used.

The term 'fermented broth including a carbonate salt of 1,5-diaminopentane', as used herein, refers to a fermented broth including a carbonate salt of 1,5-diaminopentane produced during a fermentation process. A fermented broth may be obtained by culturing a microorganism in a medium including glucose or by enzyme conversion in a fermented broth obtained by culturing a microorganism. For example, a fermented broth including a carbonate salt of 1,5-diaminopentane may be a fermented broth including a carbonate salt of 1,5-diaminopentane obtained by direct production by culturing a microorganism in a medium including glucose. For example, a fermented broth including a carbonate salt of 1,5-diaminopentane may be a fermented broth including a carbonate salt of 1,5-diaminopentane obtained by enzyme conversion using lysine dicarboxylase of lysine produced by culturing a microorganism in a medium including glucose. A type of microorganism used in production of a fermented broth including a carbonate salt of 1,5-diaminopentane is not particularly limited. Any suitable microorganism may be used, provided that the microorganism may directly produce a carbonate salt of 1,5-diaminopentane by fermentation or produce a carbonate salt of 1,5-diaminopentane by enzyme conversion.

The method may further include removing bacterial cells from the fermented broth, after the preparing of the fermented broth including the carbonate salt of 1,5-diaminopentane.

The method of removing bacterial cells from the fermented broth is not particularly limited. Any suitable method available in the art may be used. For example, a centrifugal separator, a filter press, a squeeze filter, a diatomaceous earth filter, a rotary vacuum filter, a membrane filter, and a flocculation/floatation method may be used to remove bacterial cells.

The term 'first composition', as used herein, may be a composition having 1,5-diaminopentane, as a major component, resulting from thermal decomposition of a carbonate salt of 1,5-diaminopentane by heating the fermented broth including a carbonate salt of 1,5-diaminopentane. In the preparing of the first composition, thermal decomposition of the carbonate salt of 1,5-diaminopentane may be performed at a temperature in a range of 165° C. to 175° C. for 1 to 6 hours. For example, in the preparing of the first composition, thermal decomposition of the carbonate salt of 1,5-diaminopentane may be performed at a temperature in a range of 165° C. to 174° C., 165° C. to 173° C., 165° C. to 172° C., 165° C. to 171° C., or 165° C. to 170° C. When the fermented broth including a carbonate salt of 1,5-diaminopentane is heated at a temperature in a range of 165° C. to 175° C., the carbonate salt of 1,5-diaminopentane may be thermally decomposed into 1,5-diaminopentane, carbon dioxide, and water. The carbon dioxide and water may be removed by evaporation, or the like. In the preparing of the first composition, in a case where a thermal decomposition temperature of the carbonate salt of 1,5-diaminopentane is lower than 165° C., decomposition of the carbonate salt of 1,5-diaminopentane may not be complete. Thus, a recovery rate of 1,5-diaminopentane may decrease. In the preparing of the first composition, in a case where a thermal decomposition temperature of the carbonate salt of 1,5-diaminopentane is higher than 175° C., 1,5-diaminopentane, the target product, may be thermally decomposed. Thus, a yield thereof may be deteriorated, and impurities may increase. In the preparing of the first composition, a thermal decomposition temperature of the carbonate salt of 1,5-diaminopentane in a range of 165° C. to 175° C. may be maintained for 1 hour to 6 hours, for example, 2 hours to 5 hours, and for example, 3 hours to 4 hours. When the time for a temperature of the fermented broth in a range of 165° C. to 175° C. to be maintained is excessively short, thermal decomposition of the carbonate salt of 1,5-diaminopentane may not be complete. Thus, a recovery rate of 1,5-diaminopentane may decrease. When the time for a temperature of the fermented broth in a range of 165° C. to 175° C. to be maintained is excessively long, 1,5-diaminopentane, the target product, may be thermally decomposed. Thus, a yield thereof may be deteriorated, and impurities may increase.

In the preparing of the first composition, an inert gas may be additionally provided. For example, the first composition or in a reactor containing the first composition may be provided with an inert gas. The inert gas may be, for example, nitrogen, argon, or the like. But embodiments are not limited thereto. Any suitable gas that does not oxidize 1,5-diaminopentane may be used. Due to the provision of an inert gas to the first composition or in a reactor containing the first composition, a partial pressure of carbon dioxide generated due to thermal decomposition of a carbonate salt of 1,5-diaminopentane and a partial pressure of oxygen in the air may be decreased. Therefore, thermal decomposition of a carbonate salt of 1,5-diaminopentane may be facilitated, and occurrence of a side reaction may be suppressed. In conclusion, recovery rate of 1,5-diaminopentane may improve.

The second composition and the evaporation residue may be prepared by evaporating the first composition. Any evaporation method known in the art may be used. In detail, evaporation under reduced pressure may be used. Upon reducing a pressure, the pressure may be 0.5 bar or lower, for example, 0.4 bar or lower, for example, 0.2 bar or lower, or for example, 0.1 bar or lower. Upon evaporation, a temperature of the first composition may be 90° C. or higher, for example, 100° C. or higher, for example, 110° C. or higher, or for example, 120° C. or higher. The first composition may be condensed by evaporation and may contain 1,5-diaminopentane as a major component. The evaporation residue may be a residual composition obtained by removing at least some of 1,5-diaminopentane from the first composition by evaporation under reduced pressure.

The third composition may be prepared by evaporation after addition of a solvent to the evaporation residue, and the evaporation method may be selected from known manners by one of ordinary skill in the art. Also, during evaporation under reduced pressure, the evaporator may rotate and the evaporated composition may be concentrated and obtained in a form of a concentrate or a condensate. The evaporation method may be selected depending on whether the evaporation is performed under a reduced pressure, a range of a reduced pressure, whether the evaporator rotates, or whether the third composition is concentrated. For example, the evaporation method may be selected from concentration under reduced pressure, vacuum concentration, evaporation concentration under reduced pressure, vacuum evaporation concentration, rotary evaporation concentration under reduced pressure, rotary vacuum evaporation concentration, and the like. For example, the evaporation method may be evaporation under reduced pressure. In particular, the third composition may be prepared by evaporation under reduced pressure. Upon reducing a pressure, the pressure may be 0.5 bar or lower, for example, 0.4 bar or lower, for example, 0.2 bar or lower, or for example, 0.1 bar or lower. Upon evaporation, a temperature of the evaporation residue may be 90° C. or higher, for example, 100° C. or higher, for example, 110° C. or higher, or for example, 120° C. or higher. By obtaining the third composition, after the first composition is obtained, a yield of 1,5-diaminopentane may be more improved.

When preparing the third composition, a content of a solvent added to the evaporation residue may be in a range of 80 parts to 300 parts by weight, for example, 100 parts to 280 parts by weight, or for example, 130 parts to 260 parts by weight, based on 100 parts by weight of the evaporation residue. When a content of the solvent added to the evaporation residue is excessively large, a problem, i.e., an increase in energy (steam, etc.) usage to remove water in the following distillation, may occur. When a content of the solvent added to the evaporation residue is excessively small, a problem, i.e., a low yield of 1,5-diaminopentane, may occur.

The solvent to be added to the evaporation residue may be selected from known solvents in the art by one of ordinary skill in the art. For example, the solvent may be water.

After the third composition is prepared, by-product may be recovered from the remaining residual composition. For example, after the second composition and the third composition based on 1,5-diaminopentane are separated from the first composition, by-product may be recovered from the residual composition as a remaining slurry through an additional refining process. When the slurry contains bacterial cells, distilled water may be further added to the slurry to completely dissolve the slurry to thereby separate the bacterial cells and recover by-product.

The recovering of 1,5-diaminopentane by distilling the second composition and the third composition may be recovering 1,5-diaminopentane from a mixture of the second composition and the third composition by distillation. The distillation may be performed using a method known to one of ordinary skill in the art. For example, fractional distillation, steam distillation, thin film distillation may be performed. For example, by performing fractional distillation 1,5-diaminopentane, impurities, and a solvent may be separated and recovered. For example, by performed two or more times of fractional distillations, 1,5-diaminopentane may be recovered, and the two or more times of fractional distillations may be performed consecutively or inconsecutively.

The recovering of 1,5-diaminopentane may include preparing a fourth composition containing 1,5-diaminopentane by removing a solvent from the second composition and the third composition by a first distillation; and recovering 1,5-diaminopentane from the fourth composition by a second distillation.

The fourth composition may be obtained by removing the solvent by the first distillation from the second composition and the third composition. For example, the preparing of the fourth composition may be performed in a distillation column, and a temperature of an upper part of the distillation column may be in a range of 40° C. to 50° C., for example, 44° C. to 49° C., or for example, 46° C. to 47° C. A temperature of a lower part of the distillation column may be in a range of 100° C. to 120° C., for example, 105° C. to 115° C., or for example, 110° C. to 112° C. An internal pressure of the distillation column may be in a range of 10 mmHg to 760 mmHg, for example, 40 mmHg to 600 mmHg, or for example, 60 mmHg to 200 mmHg. Under such conditions, the fourth composition including 1,5-diaminopentane may be separated at a high yield. The fourth composition including 1,5-diaminopentane may remain in a container for distillation of the second composition and the third composition, may be recovered from a lower part of the distillation column, or may be recovered from a storage pool between the distillation columns. However, embodiments are not limited thereto. Also, the fourth composition may be subjected to a secondary distillation to thereby recover 1,5-diaminopentane.

For example, the recovering of 1,5-diaminopentane may be performed in a distillation column. The fourth composition including 1,5-diaminopentane may be added through a lower part of a distillation column, however, the position through which the fourth composition is added may vary depending on specific reaction conditions and distillation column conditions.

In the recovering of 1,5-diaminopentane, a temperature of an upper part of the distillation column may be in a range of 100° C. to 120° C., for example, 105° C. to 115° C., or for example, 109° C. to 110° C. A temperature of a lower part of the distillation column may be in a range of 100° C. to 120° C., for example, 105° C. to 115° C., or for example, 110° C. to 112° C. An internal pressure of the distillation column may be in a range of 10 mmHg to 760 mmHg, for example, 40 mmHg to 600 mmHg, or for example, 60 mmHg to 200 mmHg. Under such conditions, 1,5-diaminopentane may be recovered at a high yield.

1,5-diaminopentane may be recovered in a form of a condensate in the upper part of the distillation column. For example, water and other impurities may be recovered in the lower part of the distillation column. However, embodiments are not limited thereto.

A yield of 1,5-diaminopentane recovered at the upper part of the distillation column may be 75% or higher, 80% or higher, or 95% or higher. A purity of 1,5-diaminopentane recovered at the upper part of the distillation column may be 99.90% or higher, 99.92% or higher, or 99.95% or higher.

In addition, additional refining may be included before and after the recovering of 1,5-diaminopentane by distillation from the second composition and third composition. The refining process may be performed using a method known to one of ordinary skill in the art. For example, filtration, centrifugation, anion exchange chromatography, crystallization, and high-performance liquid chromatography (HPLC) may be used.

MODE OF DISCLOSURE

The present disclosure is described in detail through the following Examples and Comparative Examples. However, these Examples are for illustrative purposes only, and the present disclosure is not intended to be limited by these Examples.

Comparative Example 1

(Fermentation)
1) Seed Culture of 1,5-Diaminopentane-Producing Bacteria 2.0 liters (L) of a medium containing 30.0 grams per liter (g/L) of glucose, 15 g/L of molasses, 1.11 g/L of phosphoric acid, 5.8 g/L of magnesium sulfate 7 hydrate, 10.0 g/L of corn steep liquor, 0.5 g/L of arginine, 1.0 mg/L of biotin, 20.0 mg/L of thiamine hydrochloride, 20.0 mg/L of calcium salt of pantothenic acid, 20.0 mg/L of nicotinic acid, and 0.2 g/L of defoamer was added to a 5-L glass fermenter. Subsequently, the medium was heated at a temperature of 120° C. for 20 minutes for sterilization. The glass fermenter was cooled to a temperature of 30° C., and *Corynebacterium glutamicum* LU11271 LdcC (Korea Patent Registration No. 10-1457229) bacterial cells grown for 12 hours in a corn meal agar (CMA) solid medium were inoculated into a sterilized medium. Subsequently, the cells were cultured at a temperature of 30° C. under sufficient aeration and stirring to obtain a seed culture.

2) Main Culture 9.0 L of a medium containing 270 g/L of glucose, 7.0 g/L of molasses, 0.7 g/L of phosphoric acid, 2.0 g/L of magnesium sulfate 7 hydrate, 5.0 g/L of corn steep liquor, 0.5 g/L of arginine, 1.0 mg/L of biotin, 20.0 mg/L of thiamine hydrochloride, 20.0 mg/L of calcium salt of pantothenic acid, 20.0 mg/L of nicotinic acid, and 0.3 g/L of defoamer was added to three 30-L stainless steel fermenters. Subsequently, the medium was heated at a temperature of 120° C. for 20 minutes for sterilization. The stainless steel fermenters were cooled to a temperature of 30° C., and 2.22 L of the seed culture prepared in Section 1) was added to each of the stainless steel fermenters to inoculate the seed culture in the sterilized medium. Subsequently, the cells were cultured at a temperature of 30° C. under sufficient aeration and stirring to obtain the main culture. Ammonia gas was supplied thereto such that a nitrogen source of the culture solution was not depleted.

Subsequently, the bacterial cells were separated and 50 kilograms (kg) of 1,5-diaminopentane fermented broth was obtained.

TABLE 1

| Component | Fermented broth (g) |
|---|---|
| Water | 37,781.0 |
| 1,5-diaminopentane | 5,150.0 |
| Ions | 165.2 |
| Bicarbonate | 6,159.8 |
| Amino acid | 37.7 |
| Organic acid | 43.1 |
| Etc. | 663.3 |
| Bacterial cells | 0 |
| Total | 50,000.0 |

(Thermal Decomposition: Removing a Carbonate Salt of 1,5-Diaminopentane)

A distillation column (available from Aceglass, perforated plate, jacketed, silvered, stage 10×3 ea) and a distillation head (available from Aceglass) at the top of the distillation column were installed on a 5-L four-neck round flask (available from Daihan Scientific Co., Ltd.). The refrigerant supplied to the distillation head was injected at 10° C. using a low-temperature constant-temperature circulating water bath (JEIO tech, Model No. HTRC-20). The heat source used was a stirring mantle (available from Misung Scientific Co., Ltd., Model No. MS-DMS639, 5 L), and heating was performed based on the temperature inside the round flask. A distillation column was connected to the inlet at the center of the 5-L four-neck round flask, and a thermometer, a gas injection device, and an injection device for the fermented broth prepared during the fermentation were installed at the other inlets, and stirring was performed using a magnetic bar (available from Cowie Co., Ltd., PTFE Oval-type stirrer bar egg, 20×40 millimeters (mm)). Both the 5 L four-neck round flask and the distillation head were equipped with a thermometer (available from Misung Scientific Co., Ltd., K type) to test the internal temperature of the round flask and the distillation column. 3,000 g of the fermented broth was added to the flask, and then 200 g of the fermented broth per each addition was sequentially further added using a pump (available from EYELA Co., Ltd., Model No. RP-2000) while thermal decomposition of the carbonate salt of 1,5-diaminopentane was carried out until the total amount of the added fermentation broth became 5,000 g. The internal temperature of the round flask was elevated from a temperature of 100° C. to 165° C. over 12 hours, and the temperature was maintained at 165° C. for 3 hours to perform thermal decomposition. Nitrogen gas was injected through a gas injection inlet connected to the gas injection device. A condensate and carbon dioxide generated from the thermal decomposition of the carbonate salt of 1,5-diaminopentane were removed from the distillation head. 3,917.3 g of the condensate and 638.4 g of the solution in the lower part of the distillation column were recovered, and 444.3 g of carbon dioxide was released into the air. Table 2 shows a composition analysis result before and after the thermal decomposition. In Table 2, 1,5-diaminopentane, amino acid, organic acid, bicarbonate, and ions were analyzed by using high-performance liquid chromatography (HPLC), and moisture analysis was performed using the Karl-Fischer moisture measurement method.

TABLE 2

| Component | Fermented broth (g) | Condensate and gas after thermal decomposition (g) | Solution in the lower part of the distillation column after thermal decomposition (g) |
|---|---|---|---|
| Water | 3,778.1 | 3,914.7 | 35.1 |
| 1,5-diaminopentane | 515.0 | 2.6 | 510.6 |
| Ions | 16.5 | — | 16.5 |
| Carbonic acid | — | 444.3 | — |
| Bicarbonate | 616.0 | — | — |
| Amino acid | 3.8 | — | 3.8 |
| Organic acid | 4.3 | — | 2.5 |
| Etc. | 66.3 | — | 69.9 |
| Total | 5,000.0 | 4,361.6 | 638.4 |

(Evaporation)

638.4 g of the solution in the lower part of the distillation column prepared during the thermal decomposition was introduced into a rotary evaporator (Model No. N-1200B available from EYELA Co., Ltd.) having a condensing tube with a volume of 1 L, and evaporation was performed under reduced pressure of 0.05 bar with an oil bath at a temperature of 120° C. After evaporation, 447.8 g of the condensate was recovered, and 190.6 g of sludge after evaporation remained in the rotary evaporator. Table 3 shows a composition analysis result after the evaporation. In Table 3, 1,5-diaminopentane, amino acid, organic acid, and ions were analyzed by using HPLC, and moisture analysis was performed using the Karl-Fischer moisture measurement method. The yield of 1,5-diaminopentane from the evaporation was 80.5%.

TABLE 3

| Component | Solution in the lower part after thermal decomposition (g) | Sludge after evaporation (g) | Condensate after evaporation (g) |
|---|---|---|---|
| Water | 35.1 | — | 35.1 |
| 1,5-diaminopentane | 510.6 | 99.6 | 411.0 |
| Ions | 16.5 | 16.5 | — |
| Amino acid | 3.8 | 3.8 | — |
| Organic acid | 2.5 | 2.2 | 0.3 |
| Etc. | 69.9 | 68.5 | 1.4 |
| Total | 638.4 | 190.6 | 447.8 |

(First Distillation: Removing Moisture)

The distillation column used during the thermal decomposition was used in the same manner. A temperature of the lower part of the distillation column was 110° C. to 112° C. and a pressure was 0.1 bar. 447.8 g of condensate after evaporation from the Evaporation was added, and the distillation head was maintained at a temperature of 46° C. to 47° C. Subsequently, 37.9 g of the distillation column condensate was removed, and 409.9 g of the solution of the lower part of the distillation column was recovered. Table 4 shows a composition analysis result after the first distillation. In Table 4, 1,5-diaminopentane was analyzed by using gas chromatography (GC, 7890A, column HP-5 available from Agilent Technologies), and the organic acid was analyzed by using HPLC. Moisture analysis was performed using the Karl-Fischer moisture measurement method.

TABLE 4

| Component | Condensate after evaporation (g) | Condensate after distillation (g) | Solution in the lower part of the distillation column after distillation (g) |
|---|---|---|---|
| Water | 35.1 | 35.0 | 0.1 |
| 1,5-diaminopentane | 411.0 | 2.8 | 408.2 |
| Organic acid | 0.3 | 0.1 | 0.2 |
| Etc. | 1.4 | — | 1.4 |
| Total | 447.8 | 37.9 | 409.9 |

(Second Distillation: Recovering 1,5-Diaminopentane)

After distillation, the condensate receiver containing the condensate was replaced, and distillation was performed under reduced pressure with a temperature of the lower part of the distillation column in a range of 110° C. to 112° C., at a pressure of 0.1 bar. A temperature of the distillation head was maintained at 109° C. to 110° C., and 406.3 g of the condensate in the distillation column was recovered. Then, 3.3 g of solution remained in the distillation column. The components were analyzed by using GC and the Karl-Fischer method. Table 5 shows the component analysis result after the second distillation. A purity of 1,5-diaminopentane was 99.94%, and a yield of 1,5-diaminopentane based on the fermented broth including a carbonate salt of 1,5-diaminopentane was 78.9%.

TABLE 5

| Component | Solution in the lower part of the distillation column after distillation (g) | Condensate after second distillation (g) | Solution in the lower part of the distillation column after second distillation (g) |
|---|---|---|---|
| Water | 0.1 | 0.1 | — |
| 1,5-diaminopentane | 408.2 | 406.3 | 1.8 |
| Organic acid | 0.2 | — | 0.2 |
| Etc. | 1.4 | 0.1 | 1.3 |
| Total | 409.9 | 406.6 | 3.3 |

Example 1: Addition of Water During Evaporation (Fermentation)

A fermented broth was prepared in the same manner as in Comparative Example (Thermal Decomposition)

Thermal decomposition was performed on 5,000 g of the fermented broth in the same manner as in Comparative Example 1.

3,914.0 g of the condensate and 641.7 g of the solution in the lower part of the distillation column were recovered, and 444.3 g of carbon dioxide was released into the air. Table 6 shows a composition analysis result before and after the thermal decomposition.

TABLE 6

| Component | Fermented broth (g) | Condensate and gas (g) | Solution in the lower part of the distillation column (g) |
|---|---|---|---|
| Water | 3,778.1 | 3,911.3 | 38.5 |
| 1,5-diaminopentane | 515.0 | 2.7 | 510.6 |
| Ions | 16.5 | — | 16.5 |
| Carbonic acid | — | 444.3 | — |
| Bicarbonate | 616.0 | — | — |
| Amino acid | 3.8 | — | 3.8 |
| Organic acid | 4.3 | — | 2.7 |
| Etc. | 66.3 | — | 69.6 |
| Total | 5,000.0 | 4,358.3 | 641.7 |

(First Evaporation)

The solution in the lower part of the distillation column prepared during the thermal decomposition was subjected to evaporation in the same manner as in Comparative Example 1 to thereby recover a condensate including water and 1,5-diaminobutane. 192.3 g of sludge remained in the rotary evaporator.

(Second Evaporation)

After the first evaporation, 250 g of distilled water was added to 192.3 g of the sludge remaining in the rotary evaporator. Subsequently, evaporation was additionally performed under reduced pressure in the same manner as in the first evaporation.

778.7 g of the condensate was recovered, and after the evaporation, 113.0 g of sludge remained in the rotary evaporator. Table 7 shows a composition analysis results of before and after the second evaporation.

TABLE 7

| Component | Solution in the lower part of the distillation column (g) | Sludge after second evaporation (g) | Condensate after second evaporation (g) |
|---|---|---|---|
| Water | 38.5 | — | 288.5 |
| 1,5-diaminopentane | 510.6 | 22.9 | 487.7 |
| Ions | 16.5 | 16.5 | — |
| Amino acid | 3.8 | 3.8 | — |
| Organic acid | 2.7 | 2.3 | 0.4 |
| Etc. | 69.6 | 69.5 | 2.1 |
| Total | 641.7 | 113.0 | 778.7 |

As compared with 80.5% yield of 1,5-diaminopentane after evaporation in Comparative Example 1 that included the first evaporation only, the yield of 1,5-diaminopentane after the second evaporation increased to 95.5% in Example 1 that further included the second evaporation.

(First Distillation: Removing Moisture)

A first distillation was performed in a distillation column in the same manner as in Comparative Example 1. 778.7 g of the evaporation condensate was added thereto, 290.2 g of the distillation column condensate was removed, and 488.5 g of the solution in the lower part of the distillation column was recovered. Table 8 shows the component analysis result after the first distillation. A temperature in the upper part of the distillation column was in a range of 45° C. to 50° C., and a temperature in the lower part of the distillation column was in a range of 110° C. to 112° C. Distillation was performed under reduced pressure of 0.1 bar.

TABLE 8

| Component | Condensate after evaporation (g) | Condensate after distillation (g) | Solution in the lower part of the distillation column after distillation (g) |
|---|---|---|---|
| Water | 288.5 | 288.2 | 0.3 |
| 1,5-diaminopentane | 487.7 | 2.0 | 485.7 |
| Organic acid | 0.4 | — | 0.4 |
| Etc. | 2.1 | — | 2.1 |
| Total | 778.7 | 290.2 | 488.5 |

(Second Distillation: Recovering 1,5-Diaminopentane)

A second distillation was performed in a distillation column in the same manner as in Comparative Example 1. 488.5 g of the distillation column condensate was recovered, and 4.3 g of the solution in the lower part of the distillation column remained. The components were analyzed by using GC and the Karl-Fischer method. Table 9 shows composition analysis results after the second distillation. A temperature in the upper part of the distillation column was in a range of 109° C. to 110° C., and a temperature in the lower part of the distillation column was in a range of 110° C. to 112° C. Distillation was performed under a reduced pressure of 0.1 bar.

A purity of 1,5-diaminopentane in the recovered condensate was 99.90%, and a yield thereof was 93.9%. As compared with the yield of 1,5-diaminopentane in Comparative Example 1, that is, 78.9%, the yield was increased by 15%. In the second evaporation, 1,5-diaminopentane remaining in the rotary evaporator was further evaporated, thereby increasing the yield of 1,5-diaminopentane.

TABLE 9

| Component | Solution in the lower part of the distillation column after distillation (g) | Condensate after second distillation (g) | Solution in the lower part of the distillation column after second distillation (g) |
|---|---|---|---|
| Water | 0.3 | 0.3 | — |
| 1,5-diaminopentane | 485.7 | 483.7 | 2.0 |
| Organic acid | 0.4 | — | 0.4 |
| Etc. | 2.1 | 0.2 | 1.9 |
| Total | 488.5 | 484.2 | 4.3 |

Example 2: Addition of Water During Evaporation

Example 2 was performed in the same manner as in Example 1, except that 300 g of distilled water was added to 195.1 g of sludge remaining in the rotary evaporator during the second evaporation.

A purity of 1,5-diaminopentane in the final condensate recovered from the second distillation was 99.94%, and a yield thereof was 93.1%.

Example 3: Addition of Water During Evaporation

Example 3 was performed in the same manner as in Example 1, except that 350 g of distilled water was added to 190.1 g of sludge remaining in the rotary evaporator during the second evaporation.

A purity of 1,5-diaminopentane in the final condensate recovered from the second distillation was 99.93%, and a yield thereof was 93.5%.

Example 4: Addition of Water During Evaporation

Example 4 was performed in the same manner as in Example 1, except that 250 g of distilled water was added twice (i.e., 500 g of distilled water in total was added) to 193.4 g of sludge remaining in the rotary evaporator during the second evaporation.

A purity of 1,5-diaminopentane in the final condensate recovered from the second distillation was 99.90%, and a yield thereof was 95.1%.

Example 5: Thermal Decomposition Temperature Changed to 175° C.

Thermal decomposition was performed in the same manner as in Example 1, except that during the thermal decomposition, an internal temperature of the round flask was raised to 175° C. and maintained for 3 hours.

A purity of 1,5-diaminopentane in the final condensate recovered from the second distillation was 99.95%, and a yield thereof was 82.1%.

Comparative Example 2: Without Supplying Nitrogen (Fermentation)

A fermented broth was prepared in the same manner as in Comparative Example 1.

(Thermal Decomposition)

Thermal decomposition was performed in the same manner as in Comparative Example 1, except that 5,000 g of fermented broth was added to the lower part of the distillation column, and nitrogen gas was not added.

3,919.5 g of the condensate and 636.2 g of the solution in the lower part of the distillation column were recovered, and 444.3 g of carbon dioxide was released into the air. Table 10 shows composition analysis results of before and after the thermal decomposition.

TABLE 10

| Component | Fermented broth (g) | Condensate and gas after thermal decomposition (g) | Solution in the lower part of the distillation column after thermal decomposition (g) |
|---|---|---|---|
| Water | 3,778.1 | 3,914.8 | 35.0 |
| 1,5-diaminopentane | 515.0 | 4.7 | 507.5 |
| Ions | 16.5 | — | 16.5 |
| Carbonic acid | — | 444.3 | — |
| Bicarbonate | 616.0 | — | — |
| Amino acid | 3.8 | — | 3.8 |
| Organic acid | 4.3 | — | 1.5 |
| Etc. | 66.3 | — | 71.9 |
| Total | 5,000.0 | 4,363.8 | 636.2 |

(Evaporation)

Evaporation was performed in the same manner as in Comparative Example 1. 441.6 g of the condensate was recovered, and after the evaporation, 194.6 g of sludge remained in the rotary evaporator. Table 11 shows composition analysis results of before and after the evaporation.

TABLE 11

| Component | Solution in the lower part after thermal decomposition (g) | Sludge after evaporation (g) | Condensate after evaporation (g) |
|---|---|---|---|
| Water | 35.0 | — | 35.0 |
| 1,5-diaminopentane | 507.5 | 104.6 | 402.9 |
| Ions | 16.5 | 16.5 | — |
| Amino acid | 3.8 | 3.8 | — |
| Organic acid | 1.5 | 1.4 | 0.1 |
| Etc. | 71.9 | 68.3 | 3.6 |
| Total | 636.2 | 194.6 | 441.6 |

(First Distillation: Removing Moisture)

A first distillation was performed in a distillation column in the same manner as in Comparative Example 1. 441.6 g of the evaporation condensate was added thereto, 41.4 g of the distillation column condensate was removed, and 400.2 g of the solution in the lower part of the distillation column was recovered. Table 12 shows the component analysis results for after the first distillation.

TABLE 12

| Component | Condensate after evaporation (g) | Condensate after distillation (g) | Solution in the lower part of the distillation column after distillation (g) |
|---|---|---|---|
| Water | 35.0 | 34.6 | 0.4 |
| 1,5-diaminopentane | 402.9 | 6.8 | 396.1 |
| Organic acid | 0.1 | — | 0.1 |
| Etc. | 3.6 | — | 3.6 |
| Total | 441.6 | 41.4 | 400.2 |

(Second Distillation: Recovering 1,5-Diaminopentane)

A second distillation was performed in a distillation column in the same manner as in Comparative Example 1. 393.8 g of the distillation column condensate was recovered, and 6.4 g of the solution remained in the lower part of the distillation column. The components were analyzed by using GC and the Karl-Fischer method. Table 13 shows the component analysis results for after the second distillation.

A purity of 1,5-diaminopentane in the recovered condensate was 99.77%, and a yield thereof was 76.3%.

TABLE 13

| Component | Solution in the lower part of the distillation column after distillation (g) | Condensate after second distillation (g) | Solution in the lower part of the distillation column after second distillation (g) |
|---|---|---|---|
| Water | 0.4 | 0.4 | — |
| 1,5-diaminopentane | 396.1 | 392.9 | 3.2 |
| Organic acid | 0.1 | — | 0.1 |
| Etc. | 3.6 | 0.5 | 3.1 |
| Total | 400.2 | 393.8 | 6.4 |

During the thermal decomposition, when an inert gas such as nitrogen was added, oxygen and carbon dioxide were removed from the fermented broth, and thus, a side reaction did not occur. Thus, the purity of 1,5-diaminopentane was higher than 99.9%.

On the other hand, when an inert gas was not added, oxygen and carbon dioxide remaining in the fermented broth may cause a side reaction. Thus, the purity of 1,5-diaminopentane was decreased to 99.77%.

Comparative Example 3: Supplying Air Instead of Nitrogen (Fermentation)

A fermented broth was prepared in the same manner as in Comparative Example 1.

(Thermal Decomposition)

Thermal decomposition was performed in the same manner as in Comparative Example 1, except that 5,000 g of fermented broth was added to the lower part of the distillation column, and air was added instead of nitrogen gas.

3,921.1 g of the condensate and 634.6 g of the solution were recovered from the lower part of the distillation column, and 444.3 g of carbon dioxide was released into the air. Table 14 shows composition analysis results for before and after the thermal decomposition.

TABLE 14

| Component | Fermented broth (g) | Condensate and gas after thermal decomposition (g) | Solution in the lower part of the distillation column after thermal decomposition (g) |
|---|---|---|---|
| Water | 3,778.1 | 3,914.9 | 34.9 |
| 1,5-diaminopentane | 515.0 | 6.2 | 504.9 |
| Ions | 16.5 | — | 16.5 |
| Carbonic acid | — | 444.3 | — |
| Bicarbonate | 616.0 | — | — |
| Amino acid | 3.8 | — | 3.8 |
| Organic acid | 4.3 | — | 1.2 |
| Etc. | 66.3 | — | 72.5 |
| Total | 5,000.0 | 4,365.4 | 634.6 |

(Evaporation)

Evaporation was performed in the same manner as in Comparative Example 1. 449.1 g of the condensate was recovered, and after the evaporation, 185.5 g of sludge remained in the rotary evaporator. Table 15 shows composition analysis results for after the evaporation.

TABLE 15

| Component | Solution in the lower part after the thermal decomposition (g) | Sludge after evaporation (g) | Condensate after evaporation (g) |
|---|---|---|---|
| Water | 34.9 | — | 34.9 |
| 1,5-diaminopentane | 505.7 | 104.0 | 401.7 |
| Ions | 16.5 | 16.5 | — |
| Amino acid | 3.8 | 3.8 | — |
| Organic acid | 1.2 | 1.1 | 0.1 |
| Etc. | 72.5 | 60.2 | 12.3 |
| Total | 634.6 | 185.5 | 449.1 |

(First Distillation: Removing Moisture)

A first distillation was performed in a distillation column in the same manner as in Comparative Example 1. 449.1 g of the evaporation condensate was added thereto, 38.2 g of the distillation column condensate was removed, and 410.9 g of the solution was recovered from the lower part of the distillation column. Table 16 shows the component analysis results for after the first distillation.

TABLE 16

| Component | Condensate after evaporation (g) | Condensate after distillation (g) | Solution in the lower part of the distillation column after distillation (g) |
|---|---|---|---|
| Water | 34.9 | 34.5 | 0.4 |
| 1,5-diaminopentane | 401.7 | 3.7 | 398.0 |
| Organic acid | 0.1 | — | 0.1 |
| Etc. | 12.3 | — | 12.3 |
| Total | 449.1 | 38.2 | 410.9 |

(Second Distillation: Recovering 1,5-Diaminopentane)

A second distillation was performed in a distillation column in the same manner as in Comparative Example 1. 401.7 g of the distillation column condensate was recovered, and 9.3 g of the solution in the lower part of the distillation column remained. The components were analyzed by using GC and the Karl-Fischer method. Table 17 shows the component analysis results for after the second distillation.

A purity of 1,5-pentadiamine in the recovered condensate was 97.74%, and a yield thereof was 76.2%.

When air was added thereto, the purity of 1,5-diaminopentane decreased due to side reactions such as oxidation caused by oxygen in the air.

TABLE 17

| Component | Solution in the lower part of the distillation column after distillation (g) | Condensate after second distillation (g) | Solution in the lower part of the distillation column after second distillation (g) |
|---|---|---|---|
| Water | 0.4 | 0.4 | — |
| 1,5-diaminopentane | 398.0 | 392.6 | 5.5 |
| Organic acid | 0.1 | — | 0.1 |
| Etc. | 12.3 | 8.6 | 3.7 |
| Total | 410.9 | 401.6 | 9.3 |

Comparative Example 4: Low-Temperature Thermal Decomposition at 160° C.

(Fermentation)

A fermented broth was prepared in the same manner as in Comparative Example 1.

(Thermal Decomposition)

Thermal decomposition was performed on 5,000 g of the fermentation broth in the same manner as in Example 1, except that during the thermal decomposition, an internal temperature of the round flask was raised to 160° C. and maintained for 3 hours.

3,914.8 g of the condensate and 654.2 g of the solution in the lower part of the distillation column were recovered, and 444.3 g of carbon dioxide was released into the air. Table 18 shows composition analysis results for before and after the thermal decomposition.

TABLE 18

| Component | Fermented broth (g) | Condensate and gas after thermal decomposition (g) | Solution in the lower part of the distillation column after thermal decomposition (g) |
|---|---|---|---|
| Water | 3,778.1 | 3,912.2 | 32.7 |
| 1,5-diaminopentane | 515.0 | 2.6 | 510.0 |
| Ions | 16.5 | — | 16.5 |
| Carbonic acid | — | 431.0 | — |
| carbonate | — | — | 18.2 |
| Bicarbonate | 616.0 | — | — |
| Amino acid | 3.8 | — | 3.8 |
| Organic acid | 4.3 | — | 1.9 |
| Etc. | 66.3 | — | 71.2 |
| Total | 5,000.0 | 4,345.8 | 654.2 |

(Evaporation)

Evaporation was performed in the same manner as in Comparative Example 1. 414.6 g of the condensate was recovered, and after the evaporation, 239.7 g of sludge remained in the rotary evaporator. Table 19 shows composition analysis results for after the evaporation.

TABLE 19

| Component | Solution in the lower part after the thermal decomposition (g) | Sludge after evaporation (g) | Condensate after evaporation (g) |
|---|---|---|---|
| Water | 32.7 | — | 32.7 |
| 1,5-diaminopentane | 510.0 | 147.9 | 362.1 |
| Ions | 16.5 | 16.5 | — |
| carbonate | 18.2 | — | 18.2 |
| Amino acid | 3.8 | 3.8 | — |
| Organic acid | 1.9 | 1.7 | 0.2 |
| Etc. | 71.2 | 69.8 | 1.4 |
| Total | 654.2 | 239.7 | 414.6 |

(First Distillation: Removing Moisture)

A first distillation was performed in the distillation column in the same manner as in Comparative Example 1, however, during the first distillation, an excessive amount of the crystals of the carbonate salt of 1,5-diaminopentane was precipitated in the lower part of the distillation column. Thus, a second distillation was not performed.

Due to the precipitation of crystals of 1,5-diaminopentane, a yield and a purity of 1,5-diaminopentane were decreased. Therefore, when a thermal decomposition temperature is 160° C. or lower in the method of refining 1,5-diaminopentane according to one or more embodiments, a yield of 1,5-diaminopentane is significantly low Comparative Example 5: High-Temperature Thermal Decomposition at 180° C.

(Fermentation)

A fermented broth was prepared in the same manner as in Comparative Example 1.

(Thermal Decomposition)

Thermal decomposition was performed on 5,000 g of the fermentation broth in the same manner as in Example 1, except that during the thermal decomposition, an internal temperature of the round flask was raised to 180° C. and maintained for 3 hours.

3,954.8 g of the condensate and 600.9 g of the solution in the lower part of the distillation column were recovered, and 444.3 g of carbon dioxide was released into the air. Table 20 shows composition analysis results for before and after the thermal decomposition.

TABLE 20

| Component | Fermented broth (g) | Condensate and gas after thermal decomposition (g) | Solution in the lower part of the distillation column after thermal decomposition (g) |
|---|---|---|---|
| Water | 3,778.1 | 3,940.4 | 9.4 |
| 1,5-diaminopentane | 515.0 | 14.4 | 498.1 |
| Ions | 16.5 | — | 16.5 |
| Carbonic acid | — | 444.3 | — |
| carbonate | — | — | — |
| Bicarbonate | 616.0 | — | — |
| Amino acid | 3.8 | — | 3.8 |
| Organic acid | 4.3 | — | 1.9 |
| Etc. | 66.3 | — | 71.2 |
| Total | 5,000.0 | 4,399.1 | 600.9 |

(Evaporation)

Evaporation was performed in the same manner as in Comparative Example 1. 389.9 g of the condensate was recovered, and after the evaporation, 211.0 g of sludge remained in the rotary evaporator. Table 21 shows composition analysis results for after the evaporation.

TABLE 21

| Component | Solution in the lower part after the thermal decomposition (g) | Sludge after evaporation (g) | Condensate after evaporation (g) |
|---|---|---|---|
| Water | 9.4 | — | 9.4 |
| 1,5-diaminopentane | 498.1 | 123.5 | 374.6 |
| Ions | 16.5 | 16.5 | — |
| Carbonate salt | — | — | — |
| Amino acid | 3.8 | 3.8 | — |
| Organic acid | 1.9 | 1.7 | 0.2 |
| Etc. | 71.2 | 65.5 | 5.7 |
| Total | 600.9 | 211.0 | 389.9 |

(First Distillation: Removing Moisture)

A first distillation was performed in a distillation column in the same manner as in Comparative Example 1. 389.9 g of the evaporation condensate was added thereto, 10.4 g of the distillation column condensate was removed, and 379.5 g of the solution was recovered from the lower part of the distillation column. Table 22 shows composition analysis results for after the evaporation.

TABLE 22

| Component | Condensate after evaporation (g) | Condensate after distillation (g) | Solution in the lower part of the distillation column after distillation (g) |
|---|---|---|---|
| Water | 9.4 | 9.3 | 0.1 |
| 1,5-diaminopentane | 374.6 | 1.1 | 373.5 |
| Organic acid | 0.2 | — | 0.2 |
| Etc. | 5.7 | — | 5.7 |
| Total | 389.9 | 10.4 | 379.5 |

(Second Distillation: Recovering 1,5-Diaminopentane)

A second distillation was performed in a distillation column in the same manner as in Comparative Example 1. 372.6 g of the distillation column condensate was recovered, and 6.9 g of the solution remained in the lower part of the distillation column. The components were analyzed by using GC and the Karl-Fischer method. Table 23 shows the component analysis results for after the second distillation.

A purity of 1,5-pentadiamine in the recovered condensate was 99.74%, and a yield thereof was 72.2%.

When thermal decomposition was performed at a temperature of 180° C., 1,5-diaminopentane was thermally decomposed. Thus, the purity and the yield were decreased, as compared with Example 1 (purity: 99.9%, yield: 93.9%).

Also, as shown in Comparative Example 4, when thermal decomposition was performed at a temperature of 165° C., crystals of 1,5-diaminopentane were generated. Thus, the purity and the yield were decreased, as compared with Example 1 (purity: 99.9%, yield: 93.9%).

Therefore, according to the above results, it was found that a purity and a yield of 1,5-diaminopentane were significantly high when thermal decomposition was performed at a temperature in a range of 165° C. to 175° C., as compared with a case where thermal decomposition is performed at a temperature higher or lower than a range of 165° C. to 175° C. It was also found that a purity and a yield were improved by performing additional evaporation by adding a solvent after evaporation of a thermal decomposition solution.

TABLE 23

| Component | Solution in the lower part of the distillation column after distillation (g) | Distillation column condensate after second distillation (g) | Solution in the lower part of the distillation column after second distillation (g) |
|---|---|---|---|
| Water | 0.1 | 0.1 | — |
| 1,5-diaminopentane | 373.5 | 371.6 | 1.9 |
| Organic acid | 0.2 | — | 0.2 |
| Etc. | 5.7 | 0.9 | 4.8 |
| Total | 379.5 | 372.6 | 6.9 |

INDUSTRIAL AVAILABILITY

When a method of refining 1,5-diaminopentane according to one or more embodiments is used, 1,5-diaminopentane with a high purity may be obtained at a high yield.

The invention claimed is:

1. A method of refining 1,5-diaminopentane, the method comprising:
preparing a fermented broth comprising a carbonate salt of 1,5-diaminopentane;
preparing, by heating the fermented broth, a first composition in which the carbonate salt of 1,5-diaminopentane is thermally decomposed;
preparing a second composition and a first evaporation residue by evaporating the first composition;
preparing a third composition and a second evaporation residue by adding water to the first evaporation residue and then evaporating the water;
recovering 1,5-diaminopentane by distilling a combination of the second composition and the third composition; and wherein the preparing of the first composition is performed at a temperature in a range of 165° C. to 175° C.

2. The method of claim 1, wherein the carbonate salt of 1,5-diaminopentane is at least one selected from 1,5-diaminopentane carbonate and 1,5-diaminopentane bicarbonate.

3. The method of claim 1, wherein the preparing of the first composition is performed for 3 hours to 4 hours.

4. The method of claim 1, wherein an inert gas is supplied in the preparing of the first composition.

5. The method of claim 1, wherein a content of the water added to the first evaporation residue is in a range of 130 parts to 260 parts by weight, based on 100 parts by weight of the first evaporation residue.

6. The method of claim 1, wherein the recovering of 1,5-diaminopentane by distilling the combination of the second composition and the third composition comprises:
   preparing a fourth composition containing 1,5-diaminopentane by removing water from a combination of the second composition and the third composition by a first distillation; and
   recovering 1,5-diaminopentane from the fourth composition by a second distillation.

7. The method of claim 6, wherein the preparing of the fourth composition is performed in a distillation column, and a temperature of an upper part of the distillation column is in a range of 40° C. to 50° C.

8. The method of claim 1, further comprising removing bacterial cells from the fermented broth after the preparing of the fermented broth comprising the carbonate salt of 1,5-diaminopentane.

* * * * *